United States Patent [19]

Steckelberg et al.

[11] Patent Number: 5,387,716
[45] Date of Patent: Feb. 7, 1995

[54] N4-SUBSTITUTED 1-ALKOXY-2-ACYLAMINO-4-AMINOBENZENES, PROCESS FOR THEIR PREPARATION AND THEIR USE

[75] Inventors: Willi Steckelberg, Hofheim/Ts.; Peter Koch, Obertshausen, both of Germany

[73] Assignee: Cassella Aktiengesellschaft, Frankfurt am Main, Germany

[21] Appl. No.: 237,311

[22] Filed: May 3, 1994

Related U.S. Application Data

[63] Continuation of Ser. No. 987,682, Dec. 9, 1992, abandoned.

[30] Foreign Application Priority Data

Dec. 20, 1991 [DE] Germany .................. 4142132

[51] Int. Cl.⁶ .......................... C07C 235/02
[52] U.S. Cl. ................................. 564/223
[58] Field of Search .................. 564/220, 223

[56] References Cited

U.S. PATENT DOCUMENTS

| | | | |
|---|---|---|---|
| 3,629,330 | 12/1971 | Brody et al. | 564/220 |
| 4,259,261 | 3/1981 | Bugant et al. | 564/220 |
| 5,223,626 | 6/1993 | Vincze et al. | 546/329 |

FOREIGN PATENT DOCUMENTS

| | | |
|---|---|---|
| 0290384 | 11/1988 | European Pat. Off. . |
| 0370953 | 5/1990 | European Pat. Off. . |
| 2652350 | 3/1991 | France . |
| 3237004 | 4/1983 | Germany . |
| 2110229 | 6/1983 | United Kingdom . |
| 2232419 | 12/1990 | United Kingdom . |
| 2236535 | 4/1991 | United Kingdom . |

OTHER PUBLICATIONS

Chemical Abstracts 87:153415; 1977; RN 64240-59-1.
ChemList 31229; RN 63494-13-3, 1977.

*Primary Examiner*—José G. Dees
*Assistant Examiner*—Samuel Barts
*Attorney, Agent, or Firm*—Connolly & Hutz

[57] ABSTRACT

The present invention relates to compounds of the general formula I

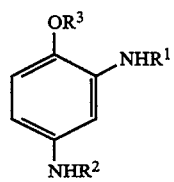

wherein
$R^1$ denotes formyl or ($C_1$-$C_3$)-alkylcarbonyl,
$R^2$ denotes the group $CH_2$—CH(A)—B, wherein A represents hydroxyl and B represents hydrogen or methyl, or A represents hydrogen and B represents hydroxymethyl, or the group COO—CH(X)—CH$_2$—D, wherein X represents hydrogen or methyl and D represents chlorine or bromine, or X represents hydrogen and D represents chloromethyl or bromomethyl, and
$R^3$ denotes ($C_1$-$C_4$)-alkyl, processes for their preparation and their use.

5 Claims, No Drawings

N4-SUBSTITUTED 1-ALKOXY-2-ACYLAMINO-4-AMINOBENZENES, PROCESS FOR THEIR PREPARATION AND THEIR USE

This application is a continuation of application Ser. No. 07/987,682 filed Dec. 9, 1992 abandoned.

The present invention relates to compounds of the general formula I

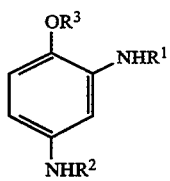

(I)

wherein
- $R^1$ denotes formyl or $(C_1-C_3)$-alkylcarbonyl,
- $R^2$ denotes the group $CH_2—CH(A)—B$, wherein A represents hydroxyl and B represents hydrogen or methyl, or A represents hydrogen and B represents hydroxymethyl, or the group $COO—CH(X)—CH_2—D$, wherein X represents hydrogen or methyl and D represents chlorine or bromine, or X represents hydrogen and D represents chloromethyl or bromomethyl, and
- $R^3$ denotes $(C_1-C_4)$-alkyl.

$(C_1-C_4)$-Alkyl is to be understood as meaning methyl, ethyl, n-propyl, i-propyl, n-butyl, sec-butyl, i-butyl and tert-butyl. The same applies analogously to $(C_1-C_3)$-alkylcarbonyl.

$R^1$ preferably denotes formyl, acetyl or propionyl.
$R^2$ preferably denotes hydroxyethyl or $COOCH_2CH_2Cl$.
$R^3$ preferably denotes methyl.

Preferred compounds of the general formula I are β-chloroethyl N-(3-acetylamino-4-methoxyphenyl)carbamate and 2-acetylamino-4-(β-hydroxyethylamino)-1-methoxybenzene.

The compounds of the general formula I can be prepared by a process in which a compound of the general formula II

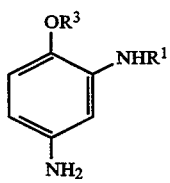

(II)

is reacted with a compound of the general formula III $$ClCOOCH(X)—CH_2—D \quad (III)$$

to give a compound of the general formula Ia

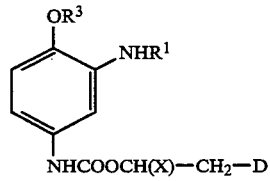

(Ia)

and, if appropriate, this is converted into a compound of the general formula Ib

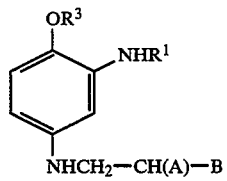

(Ib)

wherein $R^1$, $R^3$, A, B, D and X are defined as stated above.

The reaction of the compounds of the general formula II with those of the general formula III is preferably carried out by a procedure in which the compound of the general formula II is initially introduced into the reaction vessel in an inert solvent and is heated up to a temperature between room temperature and the reflux temperature, particularly preferably between 60° C. and the reflux temperature, and the compound of the general formula III is then metered into the reaction vessel in an equimolar amount or a slight excess. Suitable inert solvents are, for example, dioxane, tetrahydrofuran, ethylene glycol dimethyl ether or lower alcohols, such as methanol, ethanol or propanol. The solvents mentioned can also be employed as a mixture with water.

It is particularly preferable to carry out the reaction using an auxiliary base, which can also be initially introduced into the reaction vessel, or can be metered in continuously. Suitable auxiliary bases are, for example, alkali metal hydroxides, alkaline earth metal oxides, alkali metal and alkaline earth metal carbonates or bicarbonates and tertiary amines. Alkali metal and alkaline earth metal carbonates, such as sodium carbonate, potassium carbonate or calcium carbonate, are preferred.

If appropriate, the compounds of the general formula Ia according to the invention thus obtained can be converted into compounds of the general formula Ib according to the invention. This is effected, in particular, by treatment with a base.

Preferably, for this conversion, the compounds of the general formula Ia are initially introduced into the reaction vessel in water, an organic solvent or mixtures thereof, an alkali is added in a slight excess at room temperature, and the mixture is stirred at temperatures between 10° and 60° C., preferably between room temperature and 40° C., until the formation of the oxazolidinone which intermediately occurs (see DE-A 39 31 836) is complete. Stirring is then continued at temperatures between 40° C. and the reflux temperature until the reaction has ended. 8 to 12 hours are usually required for the entire reaction.

Suitable organic solvents are, for example, lower alcohols, such as methanol, ethanol or propanol, and water-miscible ethers, such as ethylene glycol dimethyl ether, dioxane or tetrahydrofuran.

Preferred solvents are methanol, ethanol and ethylene glycol dimethyl ether.

Suitable alkalis are sodium hydroxide solution and potassium hydroxide solution.

The starting compounds of the general formula II can be obtained in a simple manner, which is known per se, by reduction of the corresponding nitro compounds of the general formula IV

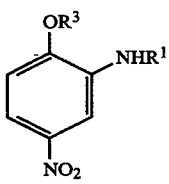

wherein $R^1$ and $R^3$ are defined as stated above.

The reduction is effected, for example, with metals of low valency or base metals, or catalytically (see, for example, EP-A 250 099, J. Am. Chem. Soc. 69 (1947) 583). Catalytic hydrogenation with customary catalysts, such as palladium-on-active-charcoal, platinum, platinum dioxide or Raney nickel, is preferred. Suitable solvents are, for example, water, lower alcohols, such as methanol, ethanol or propanol, toluene, glacial acetic acid, ethyl acetate or ether compounds, such as ethylene glycol dimethyl ether, dioxane or tetrahydrofuran.

The reaction temperature is advantageously between room temperature and 120° C., preferably between 40° and 80° C.

The reaction can be carried out under normal pressure or under an increased pressure of up to 40 bar. 10 to 30 bar are preferred. After the catalyst has been removed, the compounds of the general formula II thus obtained can be isolated in the customary manner and further processed. However, it is preferable to react them directly with the compounds of the general formula III without isolation. The solvent for this reaction is thus preferably the filtrate of the catalytic hydrogenation of the precursor.

The compounds of the general formula IV can be obtained in a simple manner, which is known per se, by reaction of a 2-amino-1-alkoxy-4-nitrobenzene with formic acid (J. Am. Chem. Soc. 103 (1981) 5599) or a carboxylic acid anhydride (EP-A 250 099; Rec. Trav. Chim. Pays-Bas 25 (1906) 18; and J. Org. Chem. 17 (1952) 1216). The temperatures of these reactions are advantageously 20° to 100° C., preferably 50° to 90° C.

It has been found, surprisingly, that if dilute carboxylic acid, that is to say 30 to 90% strength, preferably 40 to 60% strength carboxylic acid, is used as the solvent, a purification effect on the resulting compound of the general formula IV is achieved without loss of yield. It is thus possible to employ 2-amino-1-alkoxy-4-nitrobenzenes of technical grade with up to 5% by weight of isomeric impurities. After working up in the customary manner, an isomerically pure product results, the impurities remaining in the mother liquor.

The compounds of the general formula I can be used for the preparation of compounds of the general formula V

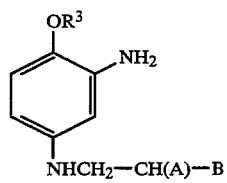

wherein $R^3$, A and B are defined as stated above, or their acid addition salts.

The compounds of the general formula V and their acid addition salts are colour couplers in oxidation dyestuffs, and play an important role, in particular, in dyeing hair and fur (see, for example, DE-A 31 32 885, DE-A 29 51 377, DE-A 36 25 916, DE-A 35 45 371, DE-A 34 41 148, DE-A 36 09 504 and DE-A 38 44 517).

The acid addition salts of the compounds of the general formula V can be formed with inorganic or organic acids, hydrogen chloride or sulphuric acid being particularly preferred. The acid addition salts can be prepared in a known manner by combining the components, advantageously in a suitable solvent or diluent. However, the compounds of the general formula V are usually obtained directly in the form of their acid addition salts during synthesis.

According to the invention, the compounds of the general formula Ib can be converted directly into compounds of the general formula V, while compounds of the general formula Ia first have to be converted into those of the general formula Ib, as stated above. However, in this case it is not necessary to isolate the compound of the general formula Ib. Rather, the deacylation can follow their synthesis directly. The deacylation of the compounds of the general formula Ib is effected in a manner which is known per se, by heating with a strong acid (see, for example, Beilsteins Handbuch der Organischen Chemie (Beilstein's Handbook of Organic Chemistry), Volume 13, Supplement III, page 1201, Springer-Verlag). Suitable acids are, in particular, sulphuric acid, hydrochloric acid and phosphoric acid.

The compound of the general formula Ib is advantageously initially introduced into the reaction vessel in water, an alcohol having 1 to 4 carbon atoms, a water-miscible ether, such as ethylene diglycol dimethyl ether, or mixtures of the solvents mentioned with one another, and is heated under reflux with an excess of the strong acid for several hours.

By providing the compounds of the general formula I according to the invention, an advantageous process for the preparation of the compounds of the general formula V starting from 2-amino-1-alkoxy-4-nitrobenzenes is thus also available.

For example, 2-amino-4-hydroxy-ethylamino-1-methoxybenzene can be prepared, starting from commercially available 2-amino-4-nitro-1-methoxybenzene via the compounds according to the invention β-chloroethyl N-(3-acetylamino-4-methoxyphenyl)carbamate and 2-acetylamino-4-(β-hydroxyethylamino)-1-methoxybenzene.

EXAMPLE 1

Preparation of β-chloroethyl N-(3-acetylamino-4-methoxyphenyl)carbamate a) 2-Acetylamino-4-nitro-1-methoxybenzene 504 g (3 mol) of 2-amino-4-nitro-1-methoxybenzene are introduced into 860 ml of acetic acid and 600 ml of water (or the combined main filtrate and first wash filtrate of a previous batch) and the mixture is heated to 80° C. 358 g (3.2 mol) of acetic anhydride are added dropwise in the course of 10 minutes. The mixture is subsequently stirred at 80° C. for 4 hours, and then cooled to room temperature, while stirring, by removing the heating bath and finally to 15° C. The pale yellow needles which have precipitated are filtered off with suction, washed with 300 ml of 60% strength acetic acid and 1500 ml of water in several portions and dried.

Yield: 592.3 g (93.6%) Melting point: 174°–175° C. Uniform according to chromatographic analyses.

b) β-Chloroethyl N-(3-acetylamino-4-methoxyphenyl)carbamate 126 g (0.6 mol) of 2-acetylamino-4-nitro-1-methoxybenzene are transferred into a stainless steel autoclave with 350 ml of ethylene glycol dimethyl ether (DME), 1.5 g of palladium-on-charcoal catalyst (10% strength) are added and catalytic hydrogenation is carried out at 60° C. under a hydrogen pressure of 20 bar. After the calculated amount of hydrogen has been absorbed, the mixture is cooled to room temperature, the catalyst is filtered off, the residue is washed with a little DME, 32.2 g (0.32 mol) of calcium carbonate are added to the filtrate and the mixture is heated to 78° C. 90 g (0.63 mol) of chloroethyl chloroformate are added dropwise in the course of three hours, the mixture is subsequently stirred at 78° C. for four hours and cooled to 30° C., and 500 ml of water and 500 ml of ice-water are added. The product is filtered off with suction, washed with 500 ml of water and dried.

Yield: 168.4 g (97.9%) Melting point: 176°–177° C. IR spectrum (KBr): $\nu=1705$ cm$^{-1}$ (C=O carbamate), 1660 cm$^{-1}$ (C=O amide), 1600 cm$^{-1}$ (C=C), 1240 cm$^{-1}$ (ether) $^1$H-NMR spectrum ([D$_6$]-DMSO): δ=2.1 (s, 3H, —COCH$_3$), 3.8 (s, 3H, —OCH$_3$), 3.9 (t, 2H, OCH$_2$—CH$_2$Cl), 4.4 (t, 2H, —OCH$_2$—CH$_2$Cl), 7.0 (m, 1H, H ar.), 7.2 (m, 1H, H ar.), 8.0 (m, 1H, H ar.), 9.1 (br. s, 1H, NH), 9.5 (br. s, 1H, NH).

EXAMPLE 2

Preparation of 2-acetylamino-4-(β-hydroxyethylamino)-1-methoxybenzene 86 g (0.3 mol) of β-chloroethyl N-(3-acetylamino-4-methoxyphenyl)carbamate are suspended in 90 ml of ethanol and 300 ml of water, 26.4 g (0.33 mol) of 50% strength sodium hydroxide solution are added, and the mixture is stirred at 30° C. for five hours. A further 75.2 g (0.66 mol) of sodium hydroxide solution are added, and the mixture is heated at 60° C. for five hours. After cooling to room temperature, the mixture is neutralised with hydrochloric acid, 200 ml of water are added and the product is isolated by filtration with suction and washing with water.

Yield: 57.4 g (85.4%) Melting point: 82°–83° C. IR spectrum (KBr): $\nu=3260$ cm$^{-1}$ (OH/NH), 1660 cm$^{-1}$ (C=O amide), 1600 cm$^{-1}$ (C=C), 1535 cm$^{-1}$ (amide II), 1225 cm$^{-1}$ (ether). $^1$H-NMR spectrum ([D$_6$]-DMSO): δ=2.1 (s, 3H, —COCH$_3$), 3.0 (dt, 2H, —CH$_2$—CH$_2$OH), 3.5 (dt, 2H, CH$_2$—CH$_2$OH), 3.7 (s, 3H, —OCH$_3$), 4.6 (t, 1H, —OH), 5.1 (t, 1H, —NH—C$_2$H$_4$OH), 6.3 (m, 1H, H ar.), 6.8 (m, 1H, H ar.), 7.4 (m, 1H, H ar.), 8.8 (br. s, 1H, NH—COCH$_3$).

EXAMPLE 3

Preparation of 2-amino-4-hydroxyethylamino-1-methoxybenzene a) from β-chloroethyl N-(3-acetylamino-4-methoxyphenyl)carbamate 86 g (0.3 mol) of β-chloroethyl N-(3-acetylamino-4-methoxyphenyl)carbamate are suspended in 90 ml of ethanol and 300 ml of water, 26.4 g (0.33 mol) of 50% strength sodium hydroxide solution are added, and the mixture is stirred at 30° C. for five hours. A further 75.2 g (0.66 mol) of sodium hydroxide solution are added and the mixture is heated at 60° C. for five hours. 85 g (0.7 mol) of 30% strength hydrochloric acid are now added to the batch and the mixture is heated under reflux for five hours. Finally, it is brought to pH 8 with sodium hydroxide solution and cooled to 10° C., and the product which has crystallised out is filtered off with suction.

Yield: 44.7 g (82%) Melting point: 99°–100° C. IR spectrum (KBr): $\nu=3300$ cm$^{-1}$ (OH/NH), 1600 cm$^{-1}$ (C=C), 1225 cm$^{-1}$ (ether), 1055/1030 cm$^{-1}$ (CH$_2$OH). $^1$H-NMR spectrum ([D$_6$]-DMSO): δ=2.9 (dt, 2H, —CH$_2$—CH$_2$—OH), 3.5 (dt, 2H, CH$_2$—CH$_2$OH), 3.6 (s, 3H, —OCH$_3$), 4.5 (br. s, 2H, —NH$_2$), 4.6 (t, 1H, —OH), 4.7 (t, 1H, —NH), 5.8 (m, 1H, H ar.), 6.0 (m, 1H, H ar.), 6.6 (m, 1H, H ar.).

b) from 2-acetylamino-4-(β-hydroxyethylamino)-1-methoxybenzene 22.4 g (0.1 mol) of 2-acetylamino-4-(β-hydroxyethylamino)-1-methoxybenzene are heated under reflux in 60 ml of water and 12.2 g (0.2 mol) of 30% strength hydrochloric acid for 5 hours. The mixture is brought to pH 8 with sodium hydroxide solution and cooled to 10° C., and the product which has crystallised out is filtered off with suction. It is washed with water and dried.

Yield: 16.4 g (90%) Physical data as under a)

We claim:

1. A compound of the general formula I

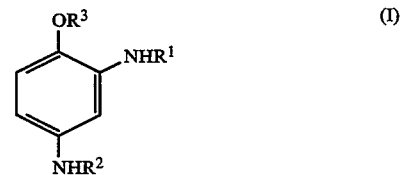

wherein

R$^1$ denotes formyl or (C$_1$–C$_3$)-alkylcarbonyl,
R$^2$ denotes hydroxyethyl, and
R$^3$ denotes (C$_1$–C$_4$)-alkyl.

2. Compounds according to claim 1, wherein R$^1$ denotes formyl, acetyl or propionyl.

3. Compounds according to claim 1, wherein R$^3$ denotes methyl.

4. Compounds according to claim 1, wherein R$^1$ denotes formyl, acetyl or proionyl, and R$^3$ denotes methyl.

5. Compound according to claim 1, wherein the compound is 2-acetylamino-4-(β-hydroxyethylamino)-1-methoxybenzene.

* * * * *